United States Patent [19]
Wilk et al.

[11] Patent Number: 5,578,031
[45] Date of Patent: Nov. 26, 1996

[54] LAPAROSCOPIC INSTRUMENT ASSEMBLY AND ASSOCIATED METHOD

[76] Inventors: Peter J. Wilk, 185 W. End Ave., New York, N.Y. 10023; Leon Pirak, 500 Mountain Ave., Springfield, N.J. 07081

[21] Appl. No.: 59,702

[22] Filed: May 10, 1993

[51] Int. Cl.$^6$ .................................................. A61B 17/36
[52] U.S. Cl. ........................... 606/49; 606/40; 606/52; 606/205; 128/898; 604/22
[58] Field of Search ................................ 606/7, 8, 13–16, 606/32, 33, 37, 39, 205–209, 40–52, 142, 143; 604/20, 21, 22; 128/898

[56] References Cited

U.S. PATENT DOCUMENTS

| | | | |
|---|---|---|---|
| 2,031,682 | 2/1936 | Wappler et al. | 606/48 |
| 3,895,636 | 7/1975 | Schmidt . | |
| 4,085,756 | 4/1978 | Weaver | 606/45 |
| 4,203,429 | 5/1980 | Vasilevsky et al. . | |
| 4,249,533 | 2/1981 | Komiya | 606/15 |
| 4,269,174 | 5/1981 | Adair | 606/49 |
| 4,524,770 | 6/1985 | Orandi | 606/46 |
| 4,655,216 | 4/1987 | Tischer | 606/51 |
| 5,074,867 | 12/1991 | Wilk . | |
| 5,084,045 | 1/1992 | Helenowski | 606/48 |
| 5,099,827 | 3/1992 | Melzer et al. | 606/142 |
| 5,176,688 | 1/1993 | Narayan et al. . | |
| 5,190,541 | 3/1993 | Abele et al. | 606/46 |

Primary Examiner—Angela D. Sykes
Assistant Examiner—Michael Peffley
Attorney, Agent, or Firm—R. Neil Sudol; Henry D. Coleman

[57] ABSTRACT

A device for use in laparoscopic surgery includes an elongate shaft having a distal end and a proximal end opposite thereto, and a pair of grasper components mounted to the shaft at the distal end thereof for grasping and holding organic tissues of a patient. The shaft is provided with a longitudinally extending channel having a distal end opening located essentially between the grasper components. A first actuator is operatively connected to the grasper components and mounted to the shaft at the proximal end thereof for actuating the grasper components to grasp and hold the tissues. An elongate rod member is slidably inserted through the channel in the instrument shaft, the rod having an operative tip at a distal end which is insertable between the grasper components when the grasper components are in an operatively closed, grasping configuration. A second actuator is operatively connected to the rod member for actuating the operative tip to perform a laparoscopic surgical procedure while the tissues are held by the grasper components. The operative tip may be designed for performing virtually any surgical operation including, but not limited to, cutting, coagulating, aspirating, taking a biopsy, suturing, stapling, and irrigating.

5 Claims, 3 Drawing Sheets

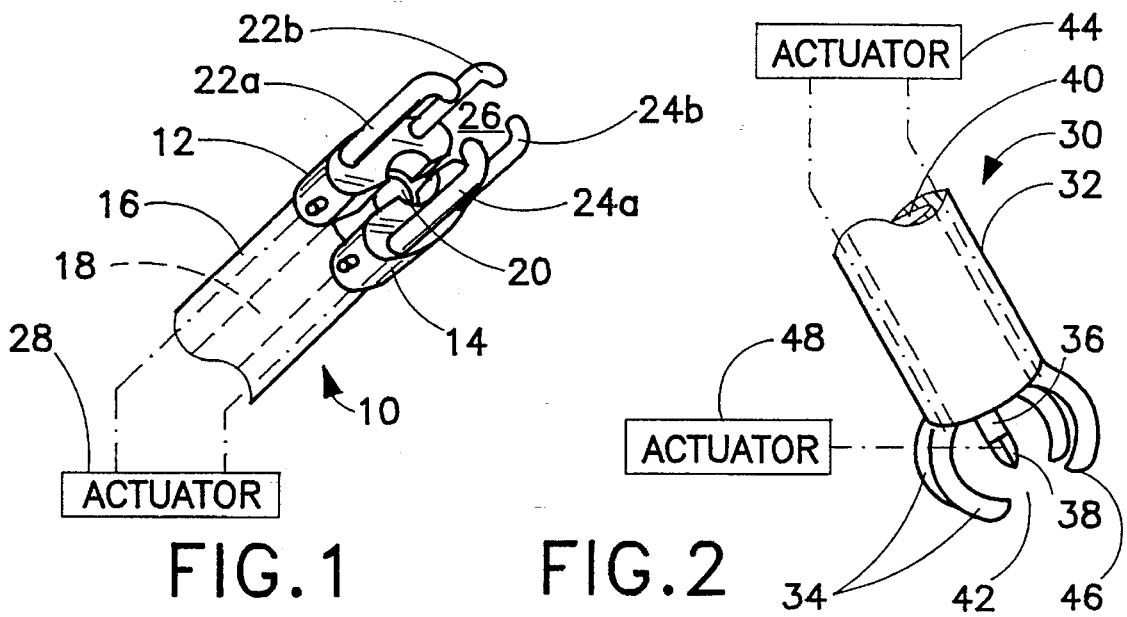
FIG. 1  FIG. 2
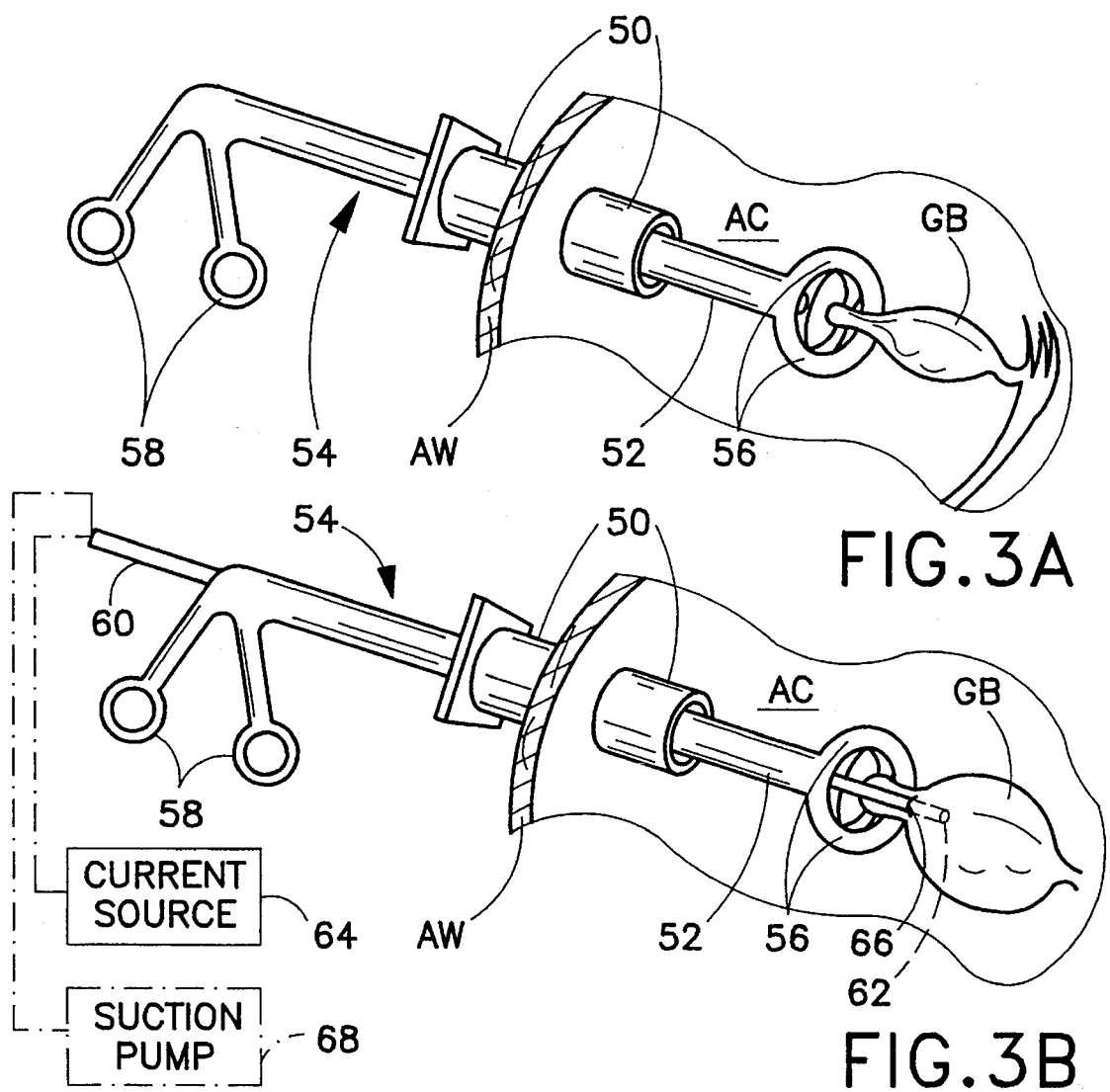
FIG. 3A
FIG. 3B

1

LAPAROSCOPIC INSTRUMENT ASSEMBLY AND ASSOCIATED METHOD

BACKGROUND OF THE INVENTION

This invention relates to a laparoscopic instrument assembly or device. This invention also relates to a laparoscopic surgical procedure. The method is useful in inserting inserting drainage tubes into internal organs, e.g., cholecystostomy tubes, cecostomy tubes, gastrostomy tubes.

Laparoscopy involves the piercing of the abdominal wall with a trocar and the insertion of a tubular trocar sleeve through the perforation. Upon a withdrawal of the trocar from the sleeve, various instruments may be inserted through the trocar sleeve to perform surgical operations inside the abdomen.

Generally, upon the disposition of the first trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Many patients require drainage of fluids from internal organs. Operations to insert drainage tubes into the gall bladder, the large intestine, and the stomach are known as cholecystostomies, cecostomies, and gastrostomies. It would be advantageous to have a simple method for performing such operations.

OBJECTS OF THE INVENTION

An object of the present invention is to provide a laparoscopic method for forming a perforation in an internal organ, e.g., for purposes of draining fluid from the organ.

Another object of the present invention is to provide such a laparoscopic method for inserting a drainage tube into an organ.

A related object of the present invention is to provide a laparoscopic instrument assembly or device for use in inserting a drainage tube into an internal organ.

A further particular object of the present invention is to provide such a device which is simple and straightforward to use.

These and other objects of the present invention will be apparent from the drawings and detailed descriptions herein.

SUMMARY OF THE INVENTION

A device for use in laparoscopic surgery comprises, in accordance with the present invention, an elongate shaft having a distal end and a proximal end opposite thereto, a pair of grasper components mounted to the shaft at the distal end for grasping and holding organic tissues of a patient, and a first actuator operatively connected to the grasper components and mounted to the shaft at the proximal end for actuating the grasper components to grasp and hold the tissues. The device further comprises a coagulating element including a coagulating tip disposed between the grasper components for forming an aperture in the tissues held by the grasper components and for sealing blood vessels in the tissues at the aperture. A second actuator is operatively connected to the coagulating element for actuating the coagulating element to form the aperture and seal edges thereof while the tissues are held by the grasper components.

According to another feature of the present invention, the coagulating element includes a suction channel and the laparoscopic device further comprises a suction pump operatively connected to the coagulating element at a proximal end thereof for aspirating fluidic material through the suction channel from an organ upon perforation thereof by the coagulating element.

According to further features of the present invention, the coagulating element includes a rod slidably inserted through a channel in the shaft of the device. The coagulating tip emerges from a distal opening in the channel located essentially between the grasper components.

In one embodiment of the invention, the grasper components each have a plurality of inwardly turned prongs spaced from one another. The prongs form or define a gap through which the coagulating element may pass into an organ which is held by the grasping components. The prongs may be pivotably mounted to the shaft at the distal end of the shaft.

In a method for use in laparoscopic surgery in accordance with the present invention, a trocar sleeve and an instrument assembly are provided. The instrument assembly includes an elongate shaft and grasper components disposed in part at a distal end of the shaft. The instrument assembly further includes a coagulating element with a coagulating tip disposed at a distal end of the shaft for forming an aperture in the tissues held by the grasper components and for sealing blood vessels in the tissues at the aperture. The method comprises the steps of (a) positioning the trocar sleeve in an abdominal wall of a patient, (b) inserting the shaft of the instrument assembly through the trocar sleeve so that a distal end of the instrument assembly projects into an abdominal cavity of the patient, (c) manipulating the instrument assembly from outside the patient to operate the instrument assembly to grasp tissues of an organ within the abdominal cavity of the patient, and (d) actuating the instrument assembly from outside the patient to operate the coagulating element to form an aperture in the tissues of the organ held by the grasper components and to seal edges of the aperture.

Where the shaft is provided with a longitudinally extending channel and the coagulating element includes an elongate rod, the method also comprising the step of inserting the rod through the channel prior to the actuation of the coagulating element.

According to another feature of the present invention, the method further comprises the step of aspirating fluidic material from the organ upon perforation thereof by the coagulating element. In one embodiment of the invention, the rod is hollow and the aspirating is implemented through the rod. In an alternative embodiment of the invention, the aspirating is implemented by removing the coagulating rod from the channel in the instrument shaft, inserting a separate elongate aspirating instrument through the channel upon removal of the coagulating rod therefrom, and using the aspirating instrument to aspirate fluid from the organ.

According to another feature of the present invention, the method additionally comprises the steps of (i) providing a tubular member having an inflatable balloon at a distal end, (ii) removing the coagulating rod from shaft channel, (iii) upon removal of the rod from the channel, inserting the tubular member through the channel while the balloon is in a collapsed configuration and while the tissues of the organ continue to be held by the grasper components, (iv) inflating the balloon upon disposition of the balloon inside the organ, (v) operating the grasper components to release the tissues of the organ upon inflation of the balloon, and (vi) withdrawing the instrument assembly from the patient through the trocar sleeve.

Where the grasper components includes a pair of jaws pivotably connected at a distal end of the instrument assembly, the manipulating of the grasper components includes the step of pivoting the jaws to capture the subject tissues.

A method in accordance with the present invention provides the advantages of laparoscopy in performing operations such as cholecystostomies, cecostomies, and gastrostomies. Owing to relatively small incisions, trauma to the patient is reduced, recovery is accelerated and convalescence improved. Hospital stays are minimized.

A method in accordance with the present invention is particular easy to perform. Only one laparoscopic instrument assembly (other than the laparoscope) is required.

A device for use in laparoscopic surgery comprises, in accordance with a more general conceptualization of the present invention, an elongate shaft having a distal end and a proximal end opposite thereto, and a pair of grasper components mounted to the shaft at the distal end thereof for grasping and holding organic tissues of a patient. The shaft is provided with a longitudinally extending channel having a distal end opening located essentially between the grasper components. A first actuator is operatively connected to the grasper components and mounted to the shaft at the proximal end thereof for actuating the grasper components to grasp and hold the tissues. An elongate rod member is slidably inserted through the channel in the instrument shaft, the rod having an operative tip at a distal end which is insertable between the grasper components when the grasper components are in an operatively closed, grasping configuration. A second actuator is operatively connected to the rod member for actuating the operative tip to perform a laparoscopic surgical procedure while the tissues are held by the grasper components.

The rod member with its operative tip is a laparoscopic instrument which is itself part of a larger instrument assembly including the graspers. The operative tip may be designed for performing virtually any surgical operation including, but not limited to, cutting, coagulating, aspirating, taking a biopsy, suturing, stapling, and irrigating. The rod member need be rigid only to an extent sufficient to enable insertion through the channel of the grasper instrument. Accordingly, a fiberoptic laser transmission guide may be inserted for cutting and coagulating purposes.

The grasper components may define a gap or aperture substantially aligned with the channel and the opening at the distal end of the instrument shaft. In that event the operative tip of the inner instrument may be passed beyond the grasper components into the held organ.

A method for use in laparoscopic surgery comprises, in accordance with this conceptualization of the present invention, the steps of positioning a trocar sleeve in an abdominal wall of a patient, inserting the elongate shaft of the instrument assembly through the trocar sleeve so that a distal end of the instrument assembly projects into an abdominal cavity of the patient, manipulating the instrument assembly from outside the patient to grasp tissues of an organ within the abdominal cavity of the patient, sliding the rod member in a distal direction through the channel so that the operative tip impinges upon tissues held by the grasper components, and actuating the instrument assembly from outside the patient to activate the operative tip to perform a surgical operation on the tissues of the organ held by the grasper components.

As mentioned above, the surgical operation may include cutting, coagulating, aspirating, taking a biopsy, suturing, stapling, and irrigating.

An instrument assembly and associated method in accordance with the present invention facilitates the performance of many laparoscopic surgical operations by enabling two operations (grasping and some other operation) to be performed through the same laparoscopic trocar sleeve or port. Accordingly, fewer incisions are required, thus benefitting the patient. In addition, laparoscopically operating is facilitated by placing the actuators of two operations at the proximal end of the same trocar sleeve. This is easier than having to reach around to two different sleeves.

BRIEF DESCRIPTION OF THE DRAWING

FIG. 1 is a schematic perspective view, on an enlarged scale, of the distal end of a laparoscopic grasping instrument for use in performing a method in accordance with the present invention.

FIG. 2 is a schematic perspective view of the distal end of a similar laparoscopic grasping instrument, showing an inner instrument in the form of a biopsy forceps, in accordance with the present invention.

FIGS. 3A–3E are schematic perspective views showing successive stages in the performance of a laparoscopic surgical procedure in accordance with the present invention, utilizing an instrument assembly in accordance with the present invention.

DETAILED DESCRIPTION

Figure 3C:
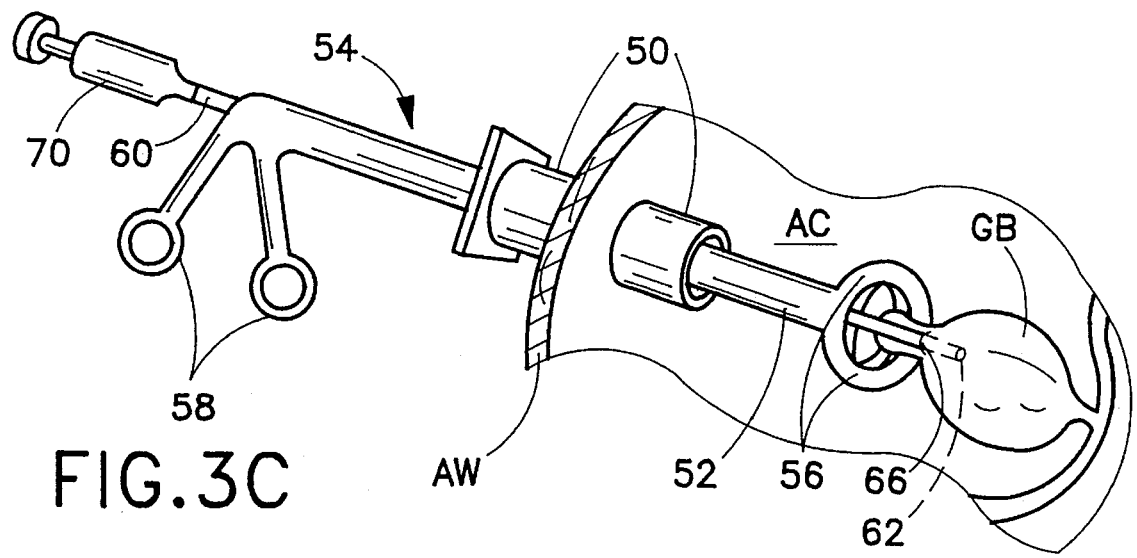

As illustrated in FIG. 1, a laparoscopic grasping instrument 10 comprises a pair of grasper components or jaw members 12 and 14 each pivotally mounted to the distal end of an elongate shaft 16 formed with a longitudinally or axially extending channel 18 having an outlet opening 20 disposed essentially between jaw members 12 and 14. Jaw members 12 and 14 each include a pair of L-shaped prongs 22a, 22b and 24a, 24b extending generally in a longitudinal direction and spaced from one another to define a gap or aperture 26 aligned with channel 18 and outlet opening 20. An actuator 28 at the proximal end of shaft 16 is operatively connected to jaw members 12 and 14 for pivoting those members between a closed grasping configuration shown in the drawing and an opening configuration.

As described hereinafter with respect to the example of FIGS. 3A–3E, laparoscopic grasping instrument 10 is insertable through a laparoscopic trocar sleeve in a laparoscopic surgical procedure to grasp tissues of an internal organ of a patient. Another elongate laparoscopic instrument such as a coagulator, a scissors, a forceps, an irrigator, a suction device, a laser transmitting fiber, etc., is inserted through channel 18 so that an operative tip of the instrument projects between jaw members 12 and 14 upon a closure thereof to grasp the tissues.

FIG. 2 shows a laparoscopic surgical instrument assembly 30 including a shaft 32 with a plurality of finger-like grasper components 34 movably mounted to the distal end of the shaft for grasping and holding tissues of an internal organ such as a gall bladder, a colon, a stomach, and a urinary bladder. A laparoscopic instrument including an elongate shaft or rod-like member 36 and an operative tip in the form of a biopsy forceps 38 is slidably inserted through a longitudinal channel 40 in shaft 32 so that forceps 38 project between grasper components 34 in a closed grasping configuration thereof. In that closed grasping configuration, grasper components 34 are spaced from one another to define an aperture or gap 42 aligned with channel 40 and an outlet opening (not shown) at a distal end thereof.

Figure 4:
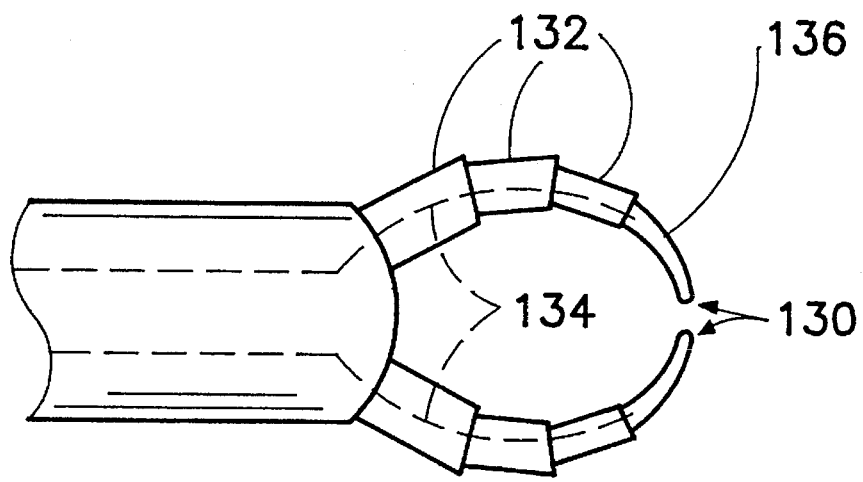
FIG. 4 is a schematic side elevational view of the distal end of another laparoscopic graspers for use in a method in accordance with the present invention.
Figure 5:
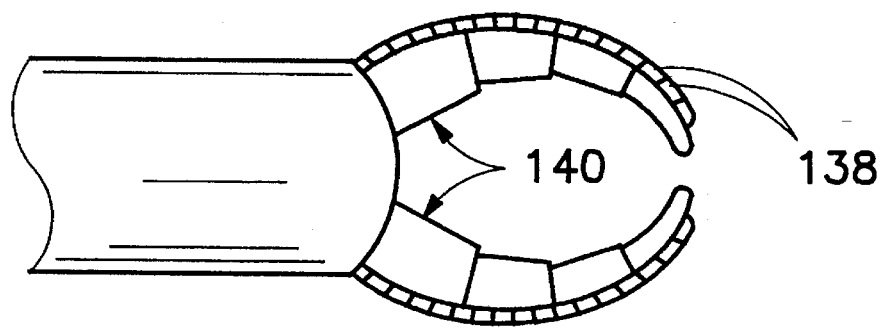
FIG. 5 is a schematic side elevational view of the distal end of a further laparoscopic graspers for use in a method in accordance with the present invention.
Figure 6:
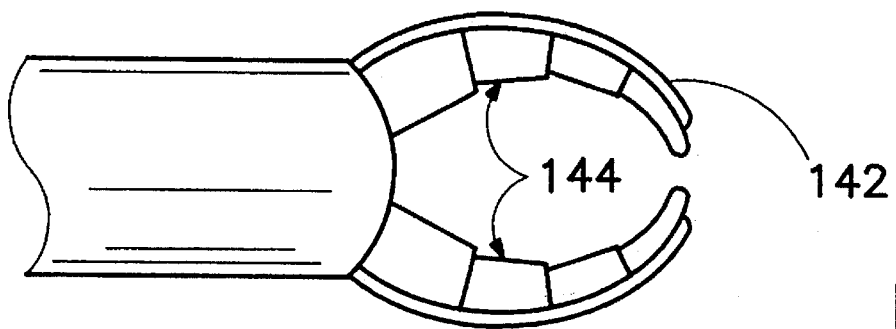
FIG. 6 is a schematic side elevational view of the distal end of yet another laparoscopic graspers for use in a method in accordance with the present invention.

Grasper components 34 may take the form of rigid fingers which are pivotably mounted to the distal end of shaft 32 and which are operatively connected to an actuator 44 at a proximal end of the instrument assembly 30. Alternatively, as illustrated in FIG. 4, grasper components 34 may take the form of articulated linkages 130 such as interfitting collars 132 which assume a substantially rigid arcuate configuration upon actuation. The actuation may be implemented by a tensile element 134 extending from a distal tip 46 (FIG. 2) or 136 (FIG. 4) of each grasper component, along an inner side thereof, or electrically by piezocrystals 138 embedded in layers along the lengths of the respective grasper fingers 140 (FIG. 5), or hydraulically by expanding small elongate bladders 142 disposed along the outer sides of grasper fingers 144 (FIG. 6).

Biopsy forceps 38 is operatively connected to an actuator 48 disposed at the proximal end of rod 36. The instrument assembly 30 of FIG. 2 is particularly useful in taking a biopsy of an organ wall which is flexible and which consequently deforms under pressure exerted by a biopsy forceps.

As illustrated in FIG. 3A, a trocar sleeve 50 is placed to traverse a skin surface of a patient such as the abdominal wall AW. An elongate hollow shaft 52 of a laparoscopic instrument assembly 54 as described hereinabove with reference to FIGS. 1 and 2 is inserted through sleeve 50 so that grasper components 56 at the distal end of the shaft 52 are inside an abdominal cavity of the patient. Actuator grips 58 at the proximal end of shaft 52 are operated to first open and then close grasper components 56 upon the gall bladder GB of the patient (FIG. 3A).

While grasper components 56 hold gall bladder GB, an elongate rod 60 is inserted through a channel (not shown) in shaft 52, as illustrated in FIG. 3B, so that an operative tip 62 in the form of a cutter/coagulator at the distal end of rod 60 emerges between grasper components 56. Upon a contact of cutter/coagulator 62 with gall bladder GB, a current source 64 is operated to enable the formation of a perforation 66 in the bladder. The tissues are coagulated by cutter/coagulator 62 which is inserted into gall bladder GB through a gap (not designated) between grasper components 56.

Figure 3D:
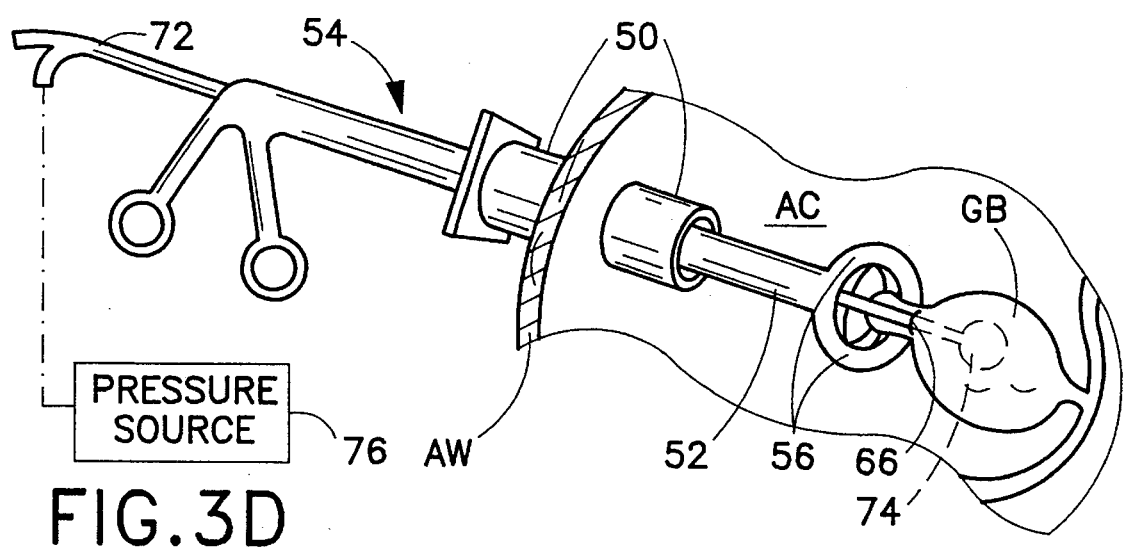

Rod 60 is preferably hollow and connected at a proximal end to a suction pump 68 (FIG. 3B) or, more specifically, a syringe 70 (FIG. 3C), whereby fluidic material (bile) in gall bladder GB may be aspirated. Upon an aspiration of bile from gall bladder GB, rod 60 is removed from shaft 52. Subsequently, a tubular member in the form of a Foley type catheter 72 is inserted through shaft 52 so that a collapsed balloon 74 at the distal end of the catheter is inserted between grasper components 56 and through perforation 66 into gall bladder GB. Balloon 74 is then inflated, as shown in FIG. 3D, by operation of a pressure source 76 such as a syringe at the proximal end of catheter 72.

Figure 3E:
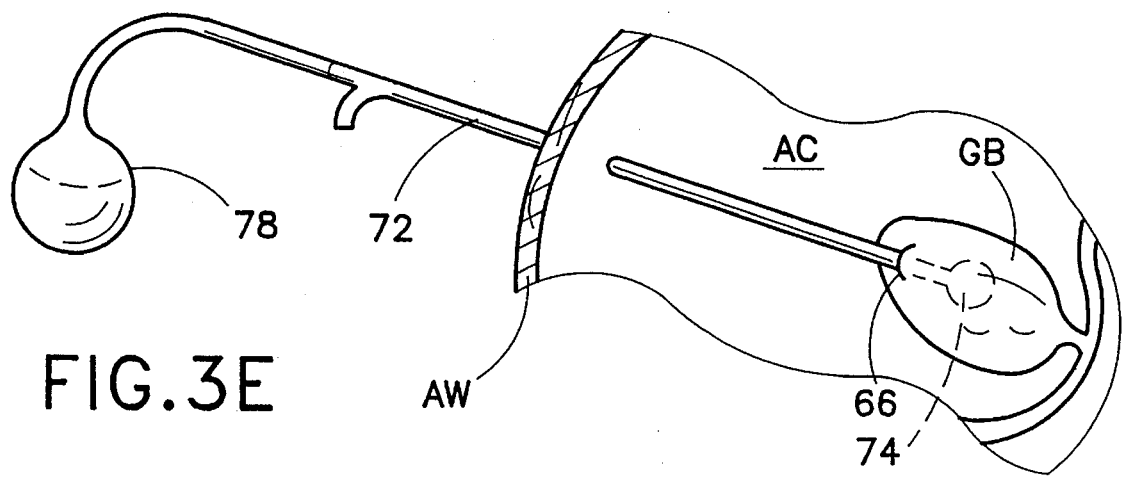

Upon the inflation of balloon 74, actuator grips 58 are operated to release gall bladder GB and instrument 54 is removed from abdominal cavity AC via trocar sleeve 50. In addition, trocar sleeve 50 is removed from abdominal wall AW. A reservoir bag 78 is then connected to the proximal end of catheter 72, as shown in FIG. 3E.

It is understood that drainage tubes may be placed in other organs such as the stomach and the intestines by the same procedure.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A method for use in laparoscopic surgery, comprising the steps of:

providing a trocar sleeve and an instrument assembly including an elongate shaft and grasping means disposed in part at a distal end of said shaft, said instrument assembly further including coagulating means with a perforating and coagulating tip disposed at a distal end of said shaft for forming an aperture in the tissues held by said grasping means and for sealing blood vessels in said tissues at said aperture;

positioning said trocar sleeve in an abdominal wall of a patient;

inserting said elongate shaft through said trocar sleeve so that a distal end of said instrument assembly projects into an abdominal cavity of the patient;

manipulating said instrument assembly from outside the patient to operate said grasping means to grasp tissues of an organ within the abdominal cavity of the patient;

actuating said instrument assembly from outside the patient to operate said coagulating means to form an aperture in the tissues of the organ held by said grasping means and to seal edges of said aperture;

aspirating fluidic material from said organ through said aperture; and maintaining a grasp on said tissues of said organ by said grasping means during said step of aspirating, said shaft being provided with a longitudinally extending channel and said coagulating means including an elongate rod, further comprising the steps of:

inserting said rod through said channel prior to said step of actuating, removing said rod from said channel prior to said step of aspirating;

providing an elongate aspirating instrument; and inserting said elongate aspirating instrument through said channel upon removal of said rod therefrom, said step of aspirating including the step of using said aspirating instrument to aspirate fluid from said organ.

2. The method defined in claim 1 wherein said grasping means includes a pair of jaws pivotably connected at a distal end of said instrument assembly, said step of manipulating including the step of pivoting said jaws to capture said tissues.

3. A method for use in laparoscopic surgery, comprising the steps of:

providing a trocar sleeve and an instrument assembly including an elongate shaft and grasping means disposed in part at a distal end of said shaft, said instrument assembly further including coagulating means with a perforating and coagulating tip disposed at a distal end of said shaft for forming an aperture in the tissues held by said grasping means and for sealing blood vessels in said tissues at said aperture;

positioning said trocar sleeve in an abdominal wall of a patient;

inserting said elongate shaft through said trocar sleeve so that distal end of said instrument assembly projects into an abdominal cavity of the patient;

manipulating said instrument assembly from outside the patient to operate said grasping means to grasp tissues of an organ within the abdominal cavity of the patient;

actuating said instrument assembly from outside the patient to operate said coagulating means to form an aperture in the tissues of the organ held by said grasping means and to seal edges of said aperture;

aspirating fluidic material from said organ through said aperture; and maintaining a grasp on said tissues of said organ by said grasping means during said step of aspirating, said shaft being provided with a longitudinally extending channel and said coagulating means including an elongate rod, further comprising the steps of:

inserting said rod through said channel prior to said step of actuating;

providing a tubular member having an inflatable balloon at a distal end;

removing said rod from channel;

upon removal of said rod from said channel, inserting said tubular member through said channel while said balloon is in a collapsed configuration and while the tissues of the organ continue to be held by said grasping means, said tubular member being inserted so that said balloon enters said organ;

upon disposition of said balloon inside said organ, inflating said balloon;

upon inflation of said balloon, operating said grasping means to release the tissues of the organ; and withdrawing the shaft from the patient through said trocar sleeve.

4. A method for use in laparoscopic surgery, comprising the steps of:

providing a trocar sleeve and an instrument assembly including an elongate shaft and grasping means disposed in part at a distal end of said shaft, said instrument assembly further including perforating and coagulating means with a perforating and coagulating tip disposed at a distal end of said shaft for forming an aperture in the tissues held by said grasping means and for sealing blood vessels in said tissues at said aperture;

positioning said trocar sleeve in an abdominal wall of a patient;

inserting said elongate shaft through said trocar sleeve so that a distal end of said instrument assembly projects into an abdominal cavity of the patient;

manipulating said instrument assembly from outside the patient to operate said grasping means to grasp tissues of an organ within the abdominal cavity of the patient;

actuating said instrument assembly from outside the patient to operate said perforating and coagulating means to form an aperture in the tissues of the organ held by said grasping means and to seal edges of said aperture;

providing a tubular member having an inflatable balloon at a distal end;

upon formation of said aperture, inserting said tubular member through a longitudinally extending channel in said shaft while said balloon is in a collapsed configuration and while the tissues of the organ continue to be held by said grasping means, said tubular member being inserted through said aperture so that said balloon enters said organ;

upon disposition of said balloon inside said organ, inflating said balloon;

upon inflation of said balloon, operating said grasping means to release the tissues of the organ; and withdrawing the shaft from the patient through said trocar sleeve.

5. The method defined in claim 4 wherein said coagulating means includes an elongate rod, further comprising the steps of inserting said rod through said channel prior to said step of actuating and removing said rod from said channel prior to said step of inserting said tubular member.

\* \* \* \* \*